United States Patent [19] [11] 4,272,848
Hoofnagle [45] Jun. 16, 1981

[54] MOISTURE-RELIEVING GARMENT

[76] Inventor: Shirley B. Hoofnagle, 309 Wessling Cir., Catonsville, Md. 21228

[21] Appl. No.: 38,888

[22] Filed: May 14, 1979

[51] Int. Cl.³ .......................... A41D 13/00; A41B 9/06
[52] U.S. Cl. ................................. 2/2; 2/69; 2/113
[58] Field of Search ...................... 2/113, 69, 406, 407, 2/403, 67, 2, 16, 22; 128/78; 3/19

[56] References Cited
U.S. PATENT DOCUMENTS

| | | | |
|---|---|---|---|
| 1,110,749 | 9/1914 | De Blieux | 2/113 |
| 1,156,757 | 10/1915 | Collett | 2/113 |
| 1,712,776 | 5/1929 | Redmond | 2/113 |
| 1,822,958 | 9/1931 | Donner | 2/67 |
| 3,397,697 | 8/1968 | Rickard | 2/406 X |
| 3,600,717 | 8/1971 | McKeehan | 3/19 |
| 3,871,367 | 3/1975 | Miller | 128/78 |
| 3,991,424 | 11/1976 | Prahl | 3/19 |
| 4,170,793 | 10/1979 | O'Brien | 2/113 |

FOREIGN PATENT DOCUMENTS 826041  12/1959  United Kingdom ........................ 3/19

OTHER PUBLICATIONS

E. I. du Pont de Nemours & Co., Memo #358, "Sontara Spunlaced Fabric", dated 3/22/76.

Primary Examiner—H. Hampton Hunter
Attorney, Agent, or Firm—J. B. Hoofnagle, Jr.

[57] ABSTRACT

A spunlaced fabric composed of random-arrayed polyester fibers is formed into a single-layer or double-layer fabric arrangement which is used to make an undergarment. The undergarment is worn by an individual and fits snugly about a selected portion of the body. For example, the undergarment could be designed to fit around the torso of the body from beneath the armpits to the hips. A rigid or semirigid outergarment, such as an orthepedic brace, is worn about the same body area, and over the undergarment, to correct a body-growth deficiency such as curvature of the spine. Relatively large beads of perspiration moisture generated beneath the brace by the individual wearing the brace are absorbed into the undergarment. The random-arrayed nature of the fibers of the fabric causes the relatively large beads of perspiration to form into mirco-droplets which migrate over the fibers and facilitate removal of the bulk of the moisture from beneath the brace.

5 Claims, 8 Drawing Figures

MOISTURE-RELIEVING GARMENT

BACKGROUND OF THE INVENTION

This invention relates to a moisture-relieving undergarment and particularly to an undergarment worn beneath a rigid or semirigid outergarment to facilitate removal of perspiration developing beneath the outergarment.

Rigid and semirigid outergarment devices are frequently worn by individuals for various purposes. For example, various types of orthepedic devices must be worn close to the body to correct deficiencies in body growth or structure. One such device is a rigid brace with slight flexibility which is worn closely about the torso of the body to correct, for example, curvature of the spine. Other devices are worn about other defective portions of the body for similar purposes. In other endeavors of life, such as in sporting events, other rigid devices, such as shoulder pads, hip pads and the like, are worn close to the body as protective devices.

In any event, such orthepedic or protective devices encompass so closely underlying portions of the body that the body tends to perspire profusely beneath the device. The captured perspiration moisture and the surrounding rigidness of the body-encompassing device results in extreme discomfort and often in skin rash and irritation in the moistened, covered area.

Various types of undergarments have been worn beneath the devices but typically result in retention of the moisture which not only results in an uncomfortable feeling but further compounds the problems of skin irritation and rashes.

SUMMARY OF THE INVENTION

The present invention contemplates an undergarment to be worn by an individual adjacent to a body portion of the individual for removal of perspiration. The undergarment is composed of a layer of fabric which is formed to fit about a selected portion of the individual's body. The fabric includes a plurality of randomly-arrayed fibers having portions which form surfaces of the fabric with one of the surfaces being adjacent to the body when the garment is worn by the individual.

DETAILED DESCRIPTION

Figure 1:
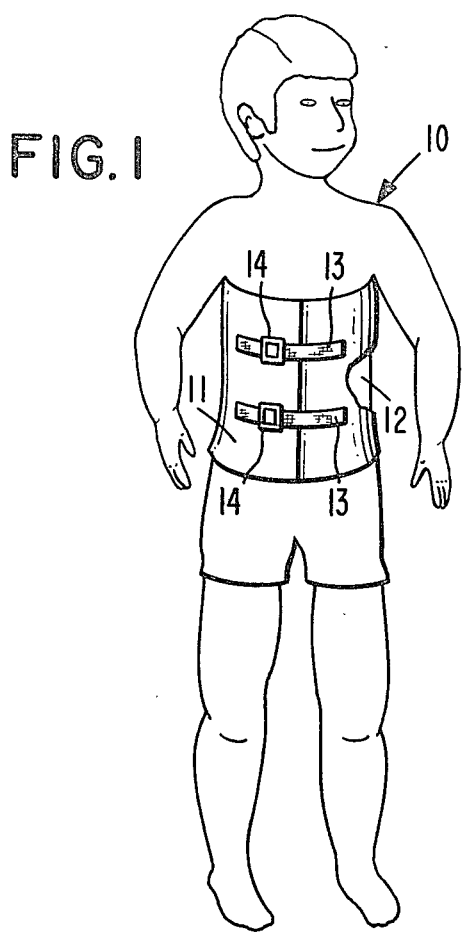
FIG. 1 is a front view showing an individual wearing an outergarment, such as a body brace, about the torso for correction of curvature of the spine.
Figure 2:
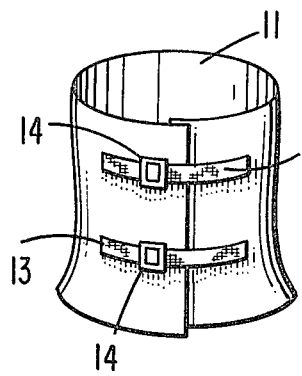
FIG. 2 is a perspective view of the body brace of FIG. 1.

During the growth of younger individuals, such as the individual 10 illustrated in FIG. 1, it is not uncommon for some individuals to begin to develop deformities in bone growth. One such deformity is curvature of the spine which is medically referred to as scoliosis. One corrective measure to insure that the deformity is arrested and the bone permitted to grow properly involves the use of a brace 11 (FIGS. 1 and 2) which is custom made for each individual. The brace 11 fits about the torso 12 of the body to apply a corrective pressure to the critical area of the spine. The particular brace 11, illustrated in FIGS. 1 and 2, is referred to as the "Wilmington" brace. Other types of braces are used to correct such a deficiency.

In order to custom manufacture the brace 11, the individual 10 is literally stretched horizontally on a rack (not shown) and plaster in a semi-fluid state is applied to the torso 12 of the stretched individual. While still in a semi-fluid state, the plaster is shaped about the individuals torso 12 and pressed firmly into position against the individuals skin and particularly in the critical area of the spine to be corrected. The combination of stretching the torso 12 and pressing the semi-fluid plaster into the region of the critical spinal area results in the formation of a rigid plaster cast (not shown) when the plaster hardens. The cast then provides an outline of rigid configuration for holding the curved spine in a corrective position for proper growth. However, the plaster cast is bulky, cumbersome and somewhat weighty.

Thereafter, the cast is separated and removed from the stretched individual 10 who is now removed from the rack. The plaster cast is then used as a mold to facilitate manufacture of the light-weight, rigid plastic brace 11 which is uniquely fitted for the particular individual 10. The brace 11, which can be composed of a polyurethane material, is sufficiently rigid to provide for the spine-straightening effect but sufficiently flexible to permit the brace to be removably placed about the torso 12 of the individual 10. Front portions of the brace 11 overlap in the front or chest area of the individual 10. Fastening straps 13 and buckles 14, which are secured at spaced locations to front portions of the brace 11, serve to facilitate firm retention of the brace about the torso 12 of the individual 10.

In order to gain effective corrective results from use of the brace 11, the individual 10 should wear the brace, for example, twenty-three hours a day and until normal spinal growth is completed. This growth period is usually completed in later teenage years. Consequently, where the deficiency is detected in pre-teen or early teenage years, which is the typical period for detection to gain maximum benefit from the brace 11, the individual 10 may be required to wear the brace for several years.

Since the brace 11 must be worn for essentially a full day and for several years, perspiration moisture beneath the brace becomes a dialy discomfort and skin irritant for the individual 10 who is wearing the brace.

In some instances, undergarments (not shown) made from conventional fabrics such as cotton or cotton blends, are worn between the brace 11 and torso 12. These undergarments tend to hold the perspiration moisture and only aggravate the condition.

Figure 3:
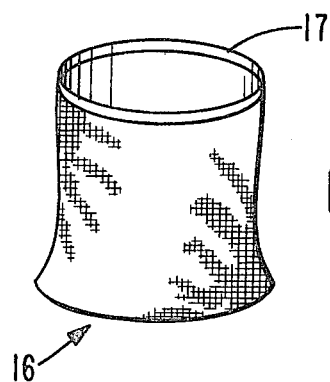
FIGS. 3, 4, and 5 are perspective views of three embodiments of an undergarment to be worn by the individual of FIG. 1 beneath the body brace to facilitate removal of perspiration from the torso area in accordance with certain principles of the invention.

To alleviate the discomfort of a wearer of the brace 11, or other type of body-hugging outergarment, an undergarment 16, as illustrated in FIG. 3, is made to fit snugly about that portion of the body of the brace wearer. For example, if the brace 11 or outergarment, is of the type which is to be worn about the torso 12 of the individual 10, the undergarment 16 is made generally in the shape of the torso. The undergarment 16 is generally of cylindrical shape, which is the shape of the preferred embodiment, and has a slight flare adjacent to a bottom end edge thereof. An elastic strip 17 is secured about a top end edge of the undergarment 16 to facilitate retention of the undergarment with the individual 10 when the undergarment is worn about the torso 12 between the armpits and the hips.

Figure 4:
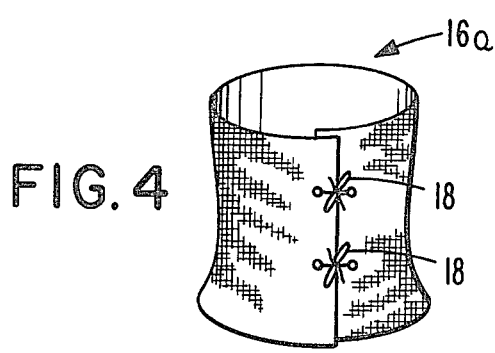
Figure 5:
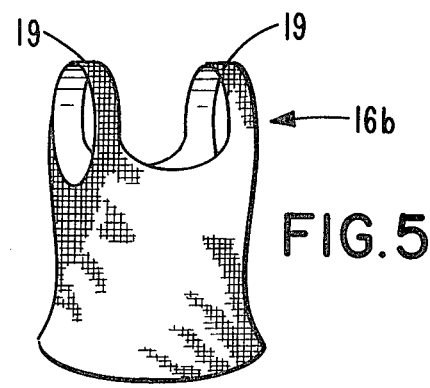

As illustrated in FIG. 4, in another embodiment, an undergarment 16a is formed in a wrap-around fashion and is provided with tie straps 18 to facilitate securing of the undergarment about the torso 12. In another embodiment (not shown) of the wrap-around undergarment 16a, the tie straps 18 are replaced with a self-gripping hook and loop-type fastener of the type distributed by Donahue Sales of 41 East 51 Street, New York, N.Y., under the registered trademark "VELCRO." In still another embodiment, as illustrated in FIG. 5, an undergarment 16b is formed in a typical undershirt fashion with shoulder straps 19 to facilitate retention of the undergarment with the individual 10.

Each of the undergarments 16 and 16b are formed in the configurations, as illustrated, by sewing together mating portions in a conventional manner.

Figure 6:
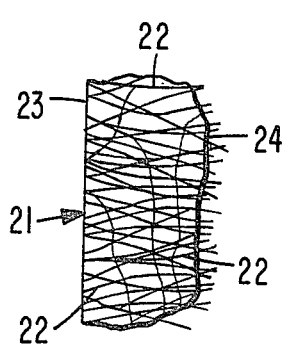
FIG. 6 is a sectional view of a fabric used to form the undergarment of FIGS. 3, 4 and 5.

As illustrated in FIG. 6, the material which forms the undergarments 16, 16a and 16b is a spunlaced fabric 21 composed of fibers 22 which are 100% polyester. The fibers 22 are entangled to form a strong structure and there are no resin binders or interfiber bonds. Thus, the fibers 22 are free to bend and move past one another as the fabric 21 is flexed and thereby provide excellent softness and draping characteristics. The fabric 21 has good resistance to tearing and does not exhibit any allergenic or toxic responses when placed in intimate contact with the human skin. Spunlaced fabrics of this type are manufactured by E. I. du Pont de Nemours and Company of Wilmington, Delaware, and are made available under their registered trademark "SONTARA." These fabrics are available in Styles 8000, 8003 and 8010. While any of these styles are suitable for the undergarments 16, 16a and 16b, Style 8010 is the preferred fabric. In the manufacture of the fabric 21, a face side 23 presents a smooth surface where the ends of the fibers 22 do not extend beyond the smooth surface. A back side 24 of the fabric 21 presents a fuzzy or unsmooth surface where the ends of at least some of the fibers 22 project outwardly from the fabric along the unsmooth surface.

Figure 7:
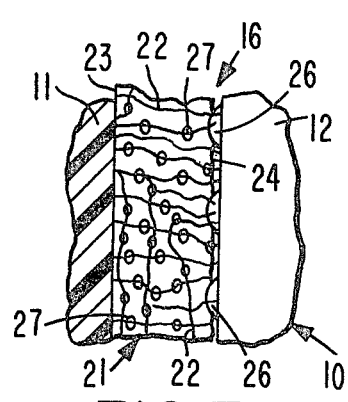
FIG. 7 is a sectional view showing one embodiment of the undergarment in accordance with certain principles of the invention and in position between the torso of the individual and the body brace of FIG. 1.

Referring to FIG. 7, in one embodiment of the undergarment 16, a portion of the undergarment is sandwiched between the torso 12 of the individual 10 and the brace 11. In a single-layer fabric arrangement, the back side 24 of the fabric 21 is placed adjacent to the skin of the individual 10. The face side 23 is placed adjacent to the inner wall of the brace 11. When relatively large beads 26 of perspiration develop on the skin of the individual 10, the beads come into contact with the ends of the fibers 22 extending from the unsmooth surface at the back side 24 of the fabric 21. Since there are ends of numerous fibers 22 projecting toward the torso 12, a plurality of such fibers will be contacted by each single bead 26 of perspiration. The multiple fiber ends cause each bead to separate into a plurality of micro-droplets 27 of moisture. The micro-droplets 27 then migrate away from the torso 12, over the fibers 22 and into the fabric 21. Since the brace 11 is not pressed against the torso 12 in an air tight arrangement, air flow will enter the space between the brace and the torso at openings of the space adjacent to the top and bottom of the brace. This air passes through the fabric 21 of the undergarment 16 and picks up moisture from the micro-droplets 27 and transports the moisture to an area outside of the space between the brace 11 and the torso 12. Since the micro-droplets 27 are relatively small, the moisture contained therein is evaporated rather quickly by the air flow through the fabric 21. Thus, perspiration generated at the torso 12 of the individual 10 is removed to greatly reduce the irritation and discomfort which would be encountered by the individual.

Figure 8:
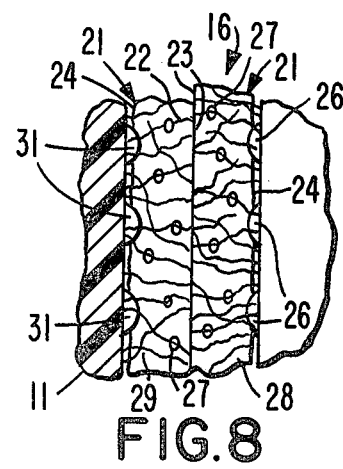
FIG. 8 is a sectional view showing the preferred embodiment of the undergarment in accordance with certain principles of the invention and in position beteen the torso of the individual and the body brace of FIGS. 1 and 2.

In the preferred embodiment of the invention as illustrated in FIG. 8, two layers 28 and 29 of the fabric 21 are secured together and used to form the cylindrically shaped undergarment 16 (FIG. 3) wherein the smooth surfaces of the front sides 23 of the layers are placed in interfacing relationship to provide a double-layer fabric arrangement. The back side 24 of layer 28 of the fabric 21 is placed adjacent to the torso 12 of the individual 10. The back side 24 of the layer 29 of fabric 21 is placed adjacent to the inner wall of the brace 11. In this double-layer fabric arrangement, the layer 28 of fabric 21 which is closest to the torso 12 functions in the same manner are previously described with respect to the single-layer embodiment of FIG. 7. As further illustrated in FIG. 8, if any beads 31 of moisture tend to collect on the inner wall of the brace 11, the ends of the fibers 22 at the unsmooth surface of the layer 29 of the fabric 21 will contact the beads to facilitate separation of the beads into micro-droplets 27. This will quickly facilitate transfer of the beads 31 of moisture, in micro-droplet form, into the fabric where the micro-droplets 27 are evaporated in the manner previously described.

The undergarments 16a and 16b will function in the same manner as the garment 16 and therefore embody the inventive concepts described hereinabove with respect to the single-layer and double-layer fabric arrangements of FIGS. 7 and 8.

Thus, the undergarments 16, 16a and 16b in the single-layer and double-layer fabric arrangements of FIGS. 7 and 8 provide continuing relief for the individual 10 by facilitating removal of perspiration developing on the body of the individual adjacent to a body-hugging outergarment, such as the brace 11, worn by the individual.

As noted above, the unsmooth surface 24 of the fabric 21 is placed adjacent to the skin of the individual 10 (FIGS. 7 and 8) and the inner wall of the brace 11 (FIG. 8). In this position, the ends of the fibers 22 protruding from the unsmooth surfaces 24 engage the beads 26 and 31 to facilitate the formation of the smaller micro-droplets 27. The single-layer fabric arrangement of FIG. 7 and the double-layer fabric arrangement of FIG. 8 can be rearranged, without departing from the spirit and scope of the invention, to place the smooth surface 23 adjacent to the skin of the individual 10 and the inner wall of the brace 11. With the smooth surfaces 23 adjacent to the individual 10 and the inner wall of the brace 11, the beads 26 and 31 engage the fibers 21 along the smooth surfaces and form the micro-droplets 27 which then migrate along the fibers as described hereinabove.

What is claimed is:

1. An undergarment to be worn by an individual between a body or limb portion of the individual and a surrounding enclosure such as an orthopedic device for removal of moisture, which comprises:

- a first single layer of fabric;
- a second single layer of fabric;
- each fabric being formed entirely by a plurality of randomly arrayed spunlaced polyester fibers;
- each fiber of each respective fabric being entangled with other fibers of the respective fabric and free to move independently of any other fiber of the respective fabric;
- at least some of the fibers of each fabric having end portions which extend outwardly from one surface of the fabric to form an unsmooth surface;
- the first layer of fabric placed in interfacing relation with the second layer of fabric to form a double-layer fabric arrangement having unsmooth outer surfaces;
- the double-layer fabric arrangement being formed in a generally cylindrical shape to fit about a selected area of the body or limb portion of the individual which area is to be encompassed by the surrounding enclosure; and
- the cylindrical shape of the double-layer fabric arrangement having opposite end edges and inner and outer surfaces formed by the unsmooth surfaces of the double-layer fabric arrangement with the inner unsmooth surface adjacent to the body or limb portion of the individual and the outer unsmooth surface adjacent to the inner surface of the surrounding enclosure when the undergarment and enclosure are worn by the individual whereby the end portions of said fibers in said unsmooth surface adjacent said body contact the moisture droplets on the wearers body and the moisture is wicked away.

2. The undergarment as set forth in claim 1, which further comprises:

an elastic strip secured about at least one end edge of the cylindrically shaped double-layer fabric arrangement to facilitate retention of the undergarment with the individual.

3. The undergarment as set forth in claim 1, which further comprises:

a pair of straps each secured at opposite ends thereof to spaced portions of one end of the cylindrically shaped double-layer fabric arrangement to be positioned over the shoulders of an individual wearing the undergarment.

4. The undergarment as set forth in claim 1 wherein the double-layer fabric arrangement is formed in a flat configuration to facilitate the wrapping thereof about the body portion in the cylindrical shape, and which further comprises means for securing the wrapped around double-layer fabric arrangement about the body portion.

5. The undergarment as set forth in claim 1 wherein one end edge of the cylindrical shape is flared to fit about an adjacent portion of the body or limb portion of the individual.

* * * * *